(12) United States Patent
Kardeis

(10) Patent No.: US 6,379,151 B1
(45) Date of Patent: Apr. 30, 2002

(54) HANDPIECE

(75) Inventor: Richard Kardeis, Bürmoos (AT)

(73) Assignee: Dentalwerk Bürmoos Gesellschaft m.b.H., Bürmoos (AT)

( * ) Notice: Subject to any disclaimer, the term of this patent is extended or adjusted under 35 U.S.C. 154(b) by 0 days.

(21) Appl. No.: 09/460,331

(22) Filed: Dec. 10, 1999

(30) Foreign Application Priority Data

Dec. 14, 1998 (AT) ................................ 2083/98

(51) Int. Cl.⁷ .......................... A61B 17/16; A61C 1/08
(52) U.S. Cl. ......................... 433/82; 433/115; 408/57
(58) Field of Search ........................ 433/82, 83, 84, 433/115, 120, 165, 166; 408/57, 59, 203.5

(56) References Cited

U.S. PATENT DOCUMENTS

| | | | |
|---|---|---|---|
| 594,329 A | * 11/1897 | Cox, Jr. | |
| 3,073,189 A | * 1/1963 | Paige | |
| 3,229,427 A | * 1/1966 | Goodhew | |
| 3,624,905 A | * 12/1971 | Barsby | |
| 4,975,056 A | * 12/1990 | Eibofner | |
| 5,141,434 A | * 8/1992 | Slaski | ......................... 433/165 |
| 5,252,065 A | * 10/1993 | Nakanishi | .................... 433/126 |
| 5,599,184 A | * 2/1997 | Field | ......................... 433/115 |

FOREIGN PATENT DOCUMENTS

| | | |
|---|---|---|
| AT | 401142 | 6/1996 |
| DE | 2331023 | 8/1978 |
| DE | 3828866 | 2/1990 |
| DE | 3930114 | 11/1990 |
| DE | 4039162 | 8/1996 |

* cited by examiner

Primary Examiner—Ralph A. Lewis
(74) Attorney, Agent, or Firm—Friedrich Kueffner (57) ABSTRACT

A medical handpiece, particularly a dental handpiece, for use with an internally cooled tool, wherein the tool has an axial hollow space into which the cooling fluid is conducted in an essentially radial direction through a bore of the tool shaft, and wherein the bore is arranged between two axially spaced apart sealing members which are arranged in the handpiece head and which seal the handpiece head relative to the tool shaft. The sealing surfaces of the sealing discs extend relative to the tool axis of the tool shaft essentially in a normal, conical or spherical direction.

9 Claims, 7 Drawing Sheets

HANDPIECE

BACKGROUND OF THE INVENTION

1. Field of the Invention

The present invention relates to a medical handpiece, particularly a dental handpiece, for use with an internally cooled tool, wherein the tool has an axial hollow space into which the cooling fluid is conducted in an essentially radial direction through a bore of the tool shaft, and wherein the bore is arranged between two axially spaced apart sealing members which are arranged in the handpiece head and which seal the handpiece head relative to the tool shaft.

2. Description of the Related Art

Handpieces of the above-described type are disclosed, for example, in DE 39 30 114 A which will be discussed in detail below.

In many fields of application, particularly when preparing deep boreholes, it is not sufficient to use cooling liquid which is applied to the outer surface of the tool and which flows downwardly along this outer surface to the work location. This is due to the thin diameters of the drilling tools, on the one hand, and the high rates of rotation which are usually used today, on the other hand, so that the cooling agent is flung from the tool before reaching the actual work location.

In addition, in conventional drills of this type, the cooling liquid to be discharged from the work location must be conducted in the same narrow annular gap as the newly added cooling liquid, but in the opposite direction, so that the liquids become mixed and the cooling effect as well as the rinsing effect for the comminuted drilling material are interrupted, so that the treatment of the tissue, usually a bone, takes place essentially uncooled and without the removal of drilling material; this is unpleasant for the patient and has medical disadvantages.

Therefore, it has already been attempted for some time to separate these two liquid flows from each other in such a way that the drilling tool is constructed so as to be hollow and the fresh cooling liquid is supplied in this hollow space and the heated cooling liquid and the comminuted drilling material is discharged through the gap between the drill and the wall of the bore hole.

This once again posed difficulties because it is necessary to force the cooling liquid in the tool head into the drill interior against the centrifugal and coriolis acceleration, without allowing significant amounts of the cooling liquid to penetrate upwardly into the drill head or downwardly out of the drill head.

The solution for this problem of arranging sealing members above and below this penetration location which would appear to be obvious is disadvantageous because of the resulting friction, because of damage to the sealing members which are usually composed of O-rings, and because of the additional drive requirement for the tool motor.

It has also been attempted to use only one sealing member, i.e., a sealing member towards the tool. This solution is disclosed, for example, in DE 38 28 866 C which shows a number of variations for introducing a cooling agent into a hollow drill. This reference also proposes to arrange O-ring sealing members at the drill shaft and to have the rotating sealing members sealingly contact the conical sealing surfaces of the handpiece head. This solution makes the drills more expensive and weakens the drills because of the required circumferential groove; also, the storage is more difficult and the occurring frictional force has a long lever arm which results in a large braking moment. Accordingly, the wear, also at the counter-surface, is high.

Other variations with fixed sealing members in the handpiece head are disclosed in DE 39 30 114 A, wherein it is also provided to supply the cooling liquid at the upper end of the tool head, so that only one sealing member is sufficient in this case. However, this measure makes it impossible to provide a push button for actuating the chucking device, and it is additionally extremely disadvantageous that the cooling liquid which still emerges is sprayed upwardly, i.e., into the field of view of the user.

A completely differently acting solution is disclosed in DE 40 39 162 C. In that case, compressed air is used which forms a pressure cushion above and below the supply location and in this manner prevents the supplied cooling liquid from entering in the axial direction along the tool shaft into the tool head or from being discharged from the tool head along the tool. The problems of this solution reside in the requirement of having to make available large quantities of air only for this purpose and to discharge the air, and also the requirement of having to extend the handpiece head in the axial direction along the tool shaft in order to make room for the necessary lines and pressure chambers.

In accordance with DE 23 31 032 C, these problems are avoided by supplying the cooling liquid to the drill in the axial direction through its upper end face, so that there are no problems with respect to the introduction of the cooling liquid against the centrifugal acceleration and coriolis acceleration, wherein a disadvantage is the fact that it is not possible to provide a push button and that in this case the cooling agent supply must be provided externally outside of the handpiece. An even greater disadvantage is the complicated threading-in of a type of needle which projects deep into the interior of the hollow drill, which is accordingly very thin and which poses enormous problems with respect to maintenance. In comparison, the fact that a sealing means is necessary at the upper head area of the handpiece is a secondary problem.

Finally, AT 401 142 B discloses the use of a sealing means of elastomer material which during operation is essentially completely lifted of f from the tool shaft under the effect of compressed air and, in a position of readiness, rests without pressure against the tool shaft, so that the braking forces due to friction and also the requirement of locking air can be reduced.

It has been found in practice that this solution, even when manufactured very precisely, does not provide the expected reliability and accuracy because of the unavoidable tolerances of the drills and particularly of the drill shafts.

SUMMARY OF THE INVENTION

Therefore, there is still a great demand for a sealing means for internally cooled drills which overcomes the problems discussed above, wherein the particular goals are a simple construction, a reliable operation and the avoidance of excessive friction.

For achieving these objects, the present invention proposes to provide essentially axially extending sealing surfaces. Specifically, the sealing surfaces of the sealing discs extend relative to the tool axis of the tool shaft essentially in a normal, conical or spherical direction.

This configuration can be achieved by providing the tool shaft in the sealing area with three different diameters which are connected to each other by shoulders, wherein two sealing discs are provided as the sealing means, and wherein each sealing disc is provided at one of the shoulders. At least one of the two sealing discs is arranged so as to be displaceable in the axial direction and the two sealing discs are mounted in the handpiece hand so as to be movable in the radial direction. The sealing discs preferably are of a material which is harder than the material of the tool shaft at the shoulders.

The present invention is based on the finding that,because of today's requirements with respect to hygiene and the material removing capacity made of the medical drills and tools, these tools are practically exclusively constructed as disposable tools; certainly, they have never a service life which exceeds a few uses.

Accordingly, the previously completely unrecognized actual reason for the problems of the previous proposals is the fact that the sealing means components mounted in the tool head are abraded or damaged by the tool, so that an exchange of the sealing means in the tool head is required even after a short period of time; this is cumbersome and can especially not be carried out by all users themselves, so that it is frequently necessary to use experts for carrying out such simple maintenance operations.

This problem is reliably prevented by the measures according to the present invention because, although the solution according to the present invention will with some probability result in abrasion effects at the tool, namely at the drill shaft in the shoulder area thereof, however, the sealing means itself will not be damaged with high reliability even after frequent uses with different tools.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
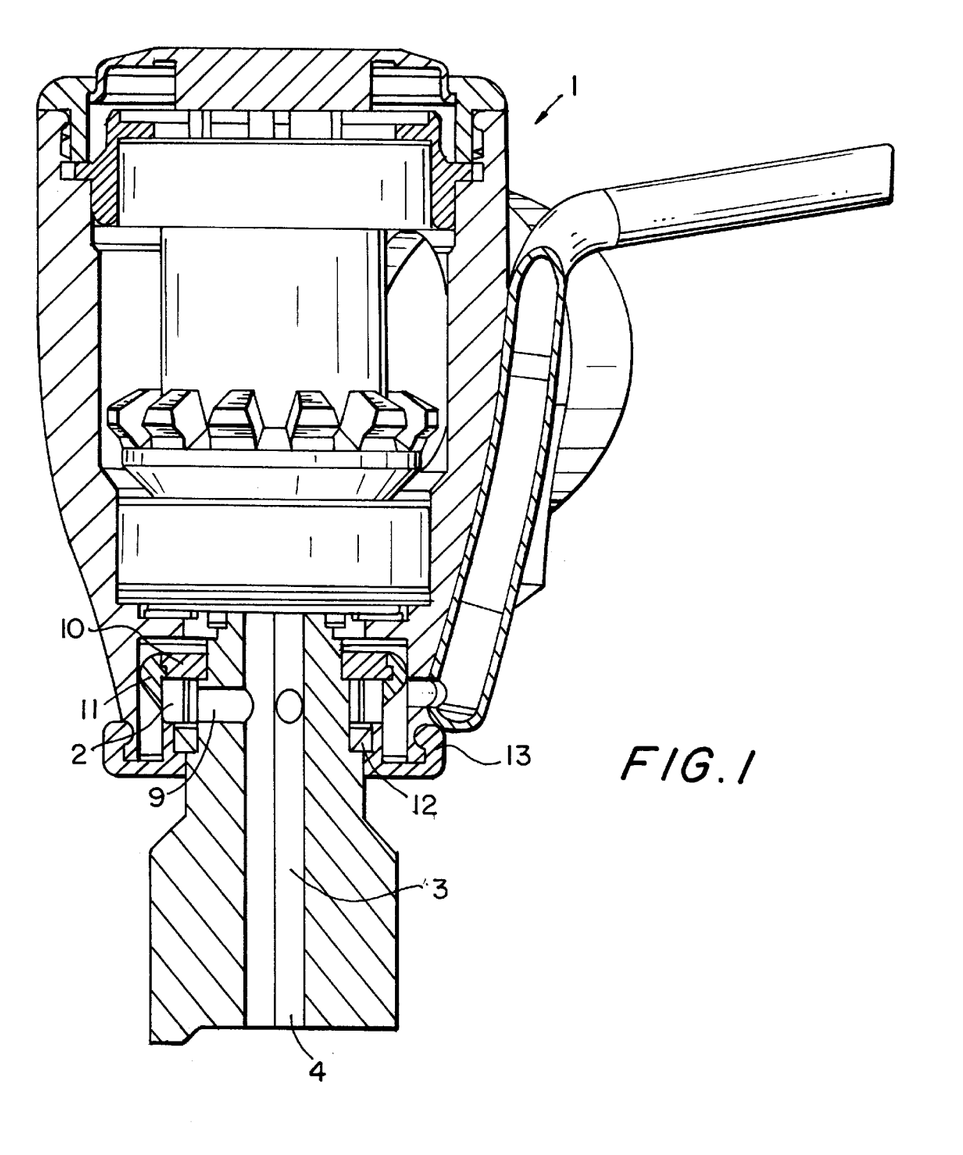
FIG. 1 is a schematic sectional view of a handpiece head according to the present invention.

FIG. 1 of the drawing is a sectional view of the head area of a handpiece equipped with a sealing means according to the present invention. Not shown in the handpiece 1 is the tool chucking device because it is not part of the invention and is not required for understanding the invention. Provided in the handpiece head 1 is a chamber 2 in which the transfer of the cooling liquid to the tool, for example, a drill 3, takes place, or from which the cooling fluid is introduced into an axial hollow space 4 of the drill 3.

The axial hollow space 4 of the drill 3 is at its end facing the tool head closed off with a precise fit in order to prevent the cooling fluid from entering the handpiece head. In most cases, the hollow space 4 is originally constructed as a throughopening and is then once again closed at the end mentioned above.

Figure 5:
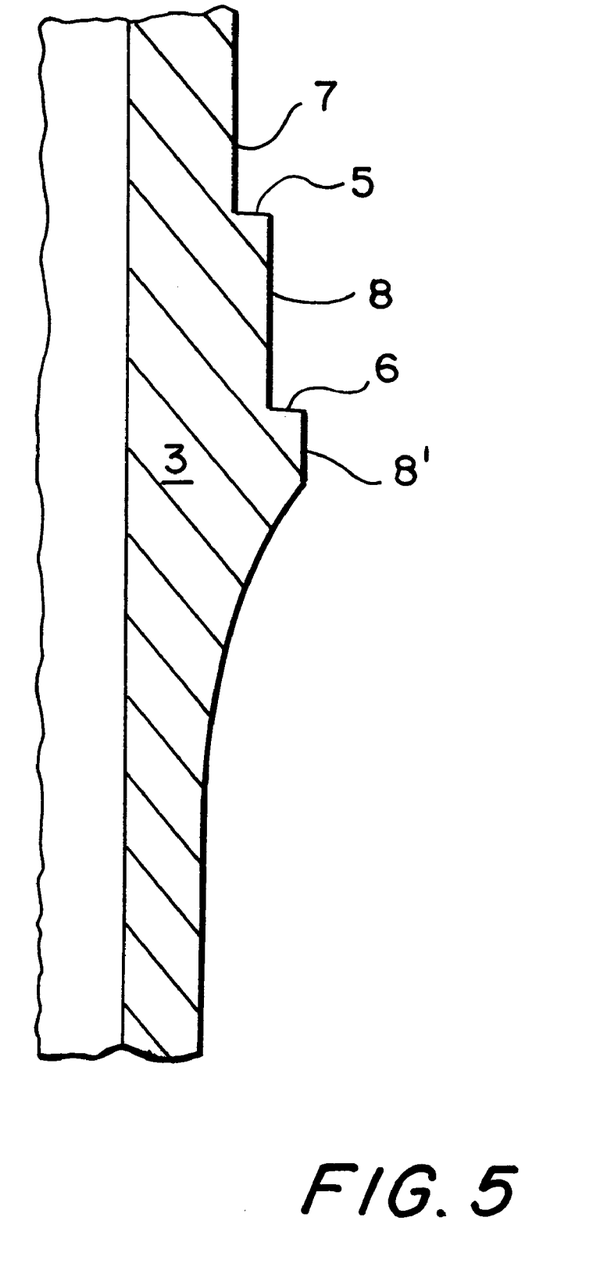
FIG. 5 is a partial sectional view of a tool shaft in the sealing area.
Figure 6:
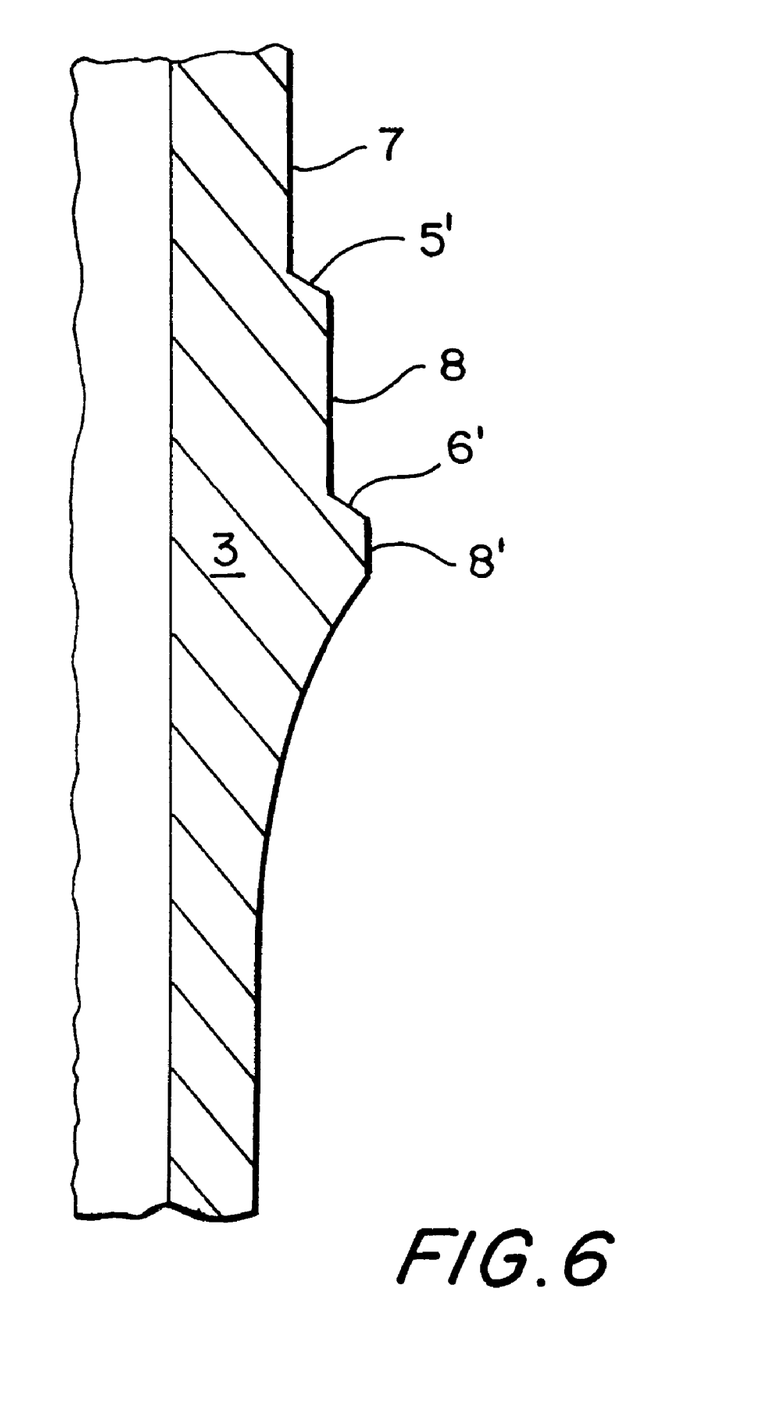
FIG. 6 is a partial sectional view of another embodiment of the tool shaft.
Figure 7:
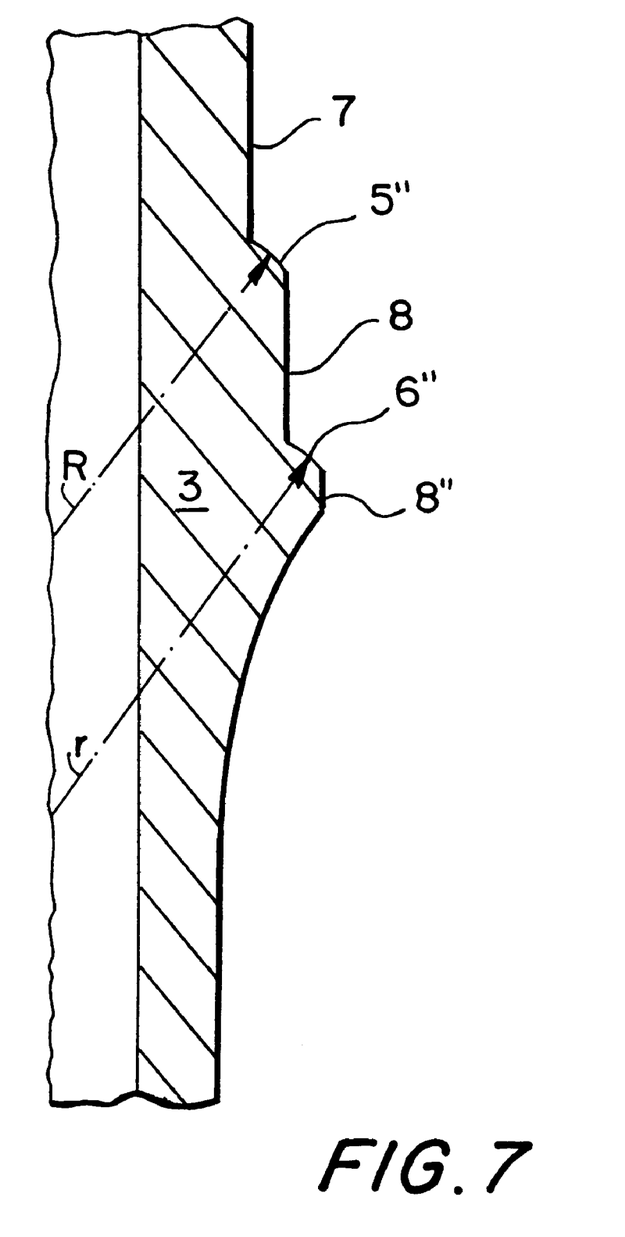
FIG. 7 is a partial sectional view of yet another embodiment of the tool shaft.

Two radial steps or shoulders 5, 6, shown in FIG. 5, are provided in the area of the drill which is located in the area of the chamber 2 of the handpiece head 1 when the drill is inserted and ready for use. These shoulders 5 and 6 connect in axial direction two cylindrical portions with different radii: a cylindrical portion 7 on the side of the shoulder 5 facing the head and having a diameter which is smaller than the diameter of the cylindrical portion 8 located on the side of the shoulder 5 facing the tool; the cylindrical portion 8 also forms the cylindrical portion arranged on the side of the shoulder 6 facing the head and its diameter is smaller than the diameter of the cylindrical portion 8' located on the side of the shoulder 6 facing the tool. Two sealing discs 10, 12 are now arranged in the handpiece head in such a way that one sealing disc interacts with the shoulder 5 and the other interacts with the shoulder 6. As seen in FIG. 5, the shoulders 5 and 6 extend in a normal direction relative to the tool axis. As seen in FIG. 6, the shoulders 5' and 6' extend in a conical direction relative to the tool axis. As seen in FIG. 7, the shoulders 5" and 6" extend in a spherical direction relative to The tool shaft 3 has a radial bore 9 which is arranged at such an axial location that it is located in the inserted state of the tool shaft between the two sealing discs 10, 12.

Figure 4:
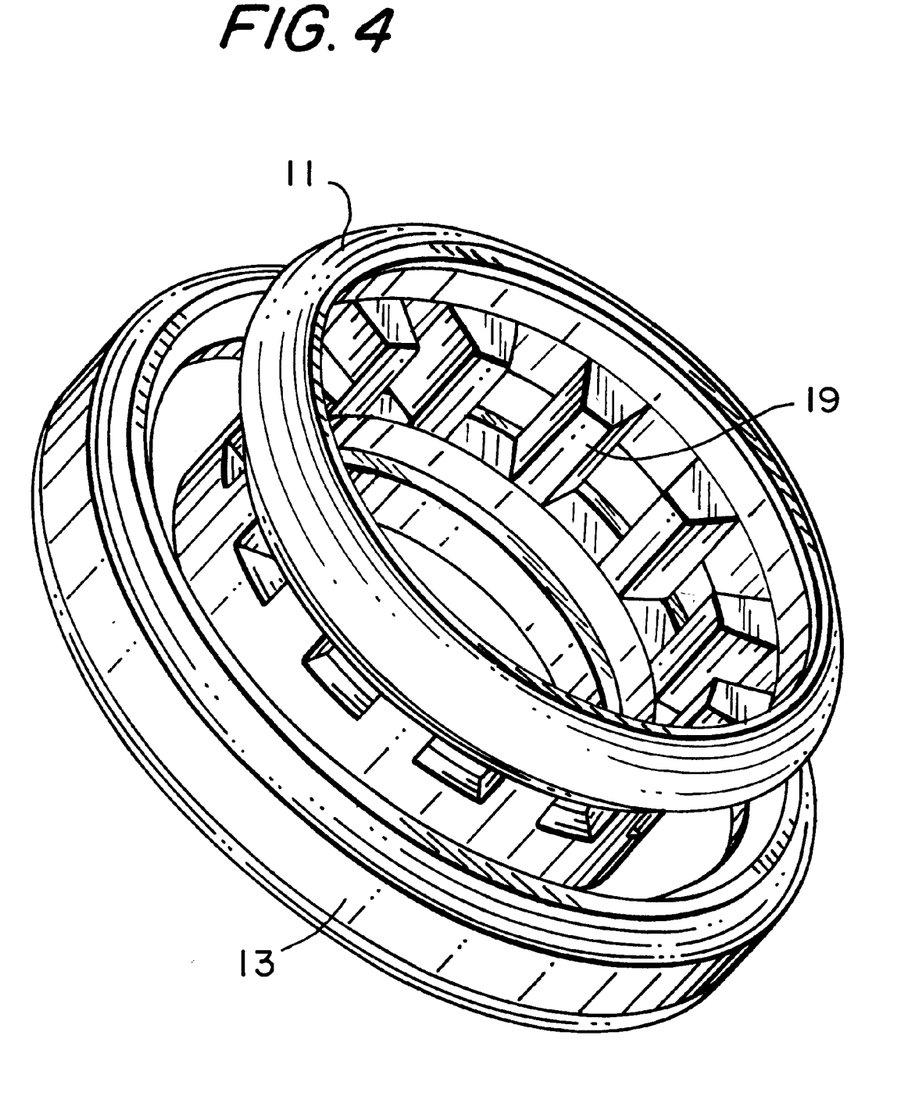
FIG. 4 is a perspective view of the sealing device of FIG. 1; [and]

In the embodiment according to FIGS. 1 and 4, the sealing ring 10 on the side of the handpiece head is mounted in an essentially toroidally-shaped elastomer support body 11, and the second sealing disc 12 on the side of the tool is supported by an elastomer ring 13 which simultaneously serves as a closing member.

As can be seen particularly in FIG. 4, the two elastomer support members 11, 13 are connected to each other through axial the tool axis. webs 19 and, thus, are integrally constructed. Of course, it is also possible to omit the axial elements and to provide two separate supports.

The support members, i.e., the support body 11 and the elastomer ring 13, serve to ensure that the sealing discs 10 and 12 are secured in the handpiece head 1 and they must also ensure that the sealing discs can yield in any desired radial direction. In this manner, it is ensured that inclined positions of the drill or any occurring eccentricities can be compensated without significantly impairing the operation of the device.

This is because it has been found that, in most cases in which the operation of conventional devices resulted very quickly to a reduction or destruction of the sealing effect, was essentially not due to excessively large diameters of the tool shafts, but to deformations and inclined positions which are unavoidable during operation.

The two elastomer support members 11, 13 also act in the axial direction on the sealing discs 10, 12 in the sense that they force the sealing discs in the direction towards the corresponding shoulder 5 or 6, respectively. This light load application or pretension results in a contact over a large area with only slight friction.

Figure 2:
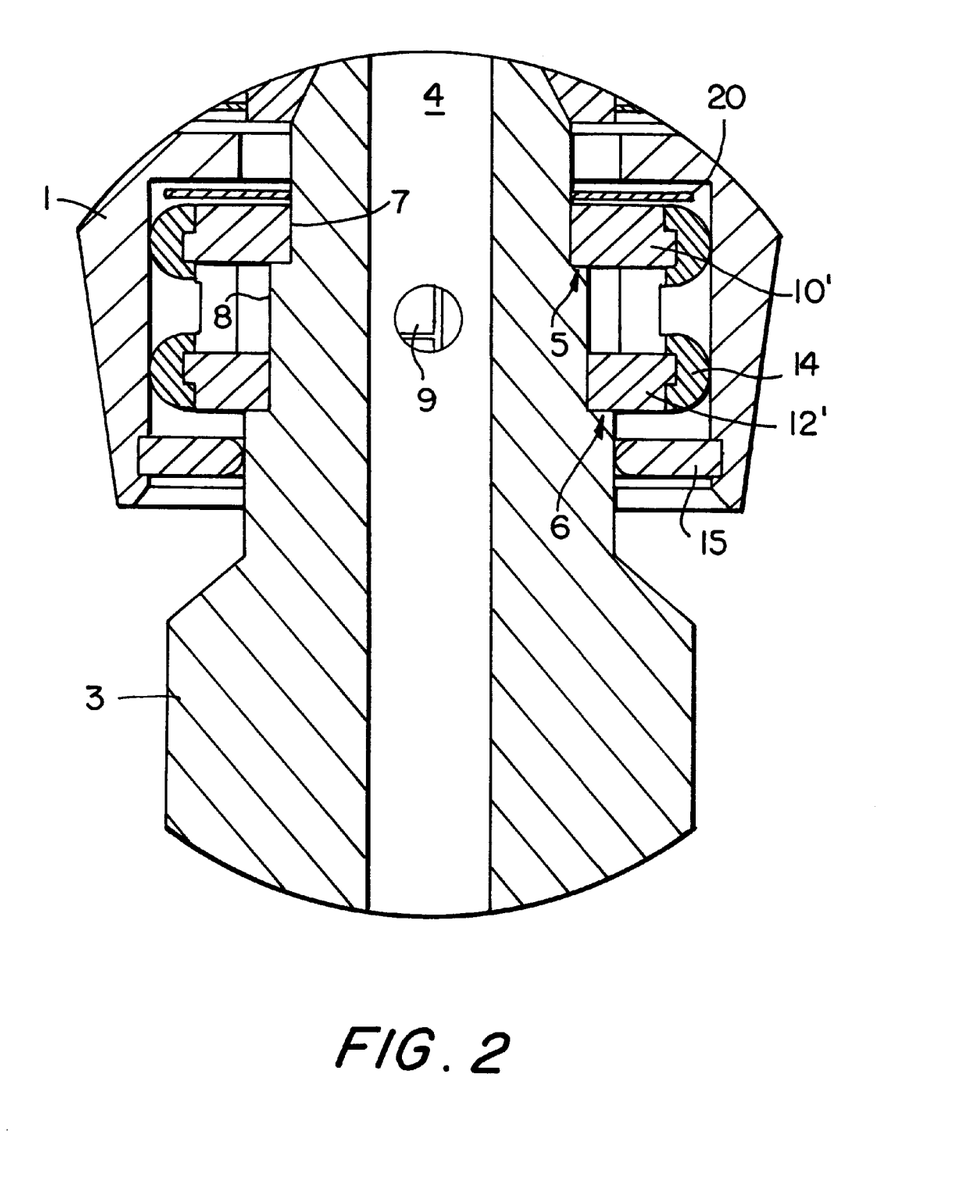
FIG. 2 is a sectional view of the sealing area of a handpiece head of another embodiment of the sealing means according to the present invention.

FIG. 2 shows on a larger scale a sealing arrangement according to the present invention similar to that of FIG. 1. FIG. 2 also clearly shows the shoulders 5, 6 of the tool shaft 3, wherein the two sealing discs 10' and 12' are of the same construction at their outer circumferences and are supported in a common elastomer support member 14 which is better visible in FIG. 3. The support member 14 secures the two sealing discs 10', 12' in the axial as well as the radial directions and makes it possible to construct the chamber to which the cooling fluid is supplied as a cylindrical space without special steps or components.

A spring 20 arranged on the side of the support member 14 facing the head presses the support member 14 downwardly, so that the sealing discs 10', 12' are pressed against their respective shoulders 5 or 6. This is facilitated by the elastomer construction of the support member 14 because if the support member 14 were rigid the spring 20 would act only on one of the two sealing discs.

In the illustrated embodiment, a closing disc 15 is provided for the head 1 of the handpiece for the mechanical protection of the handpiece, especially when the tool is removed.

Figure 3:
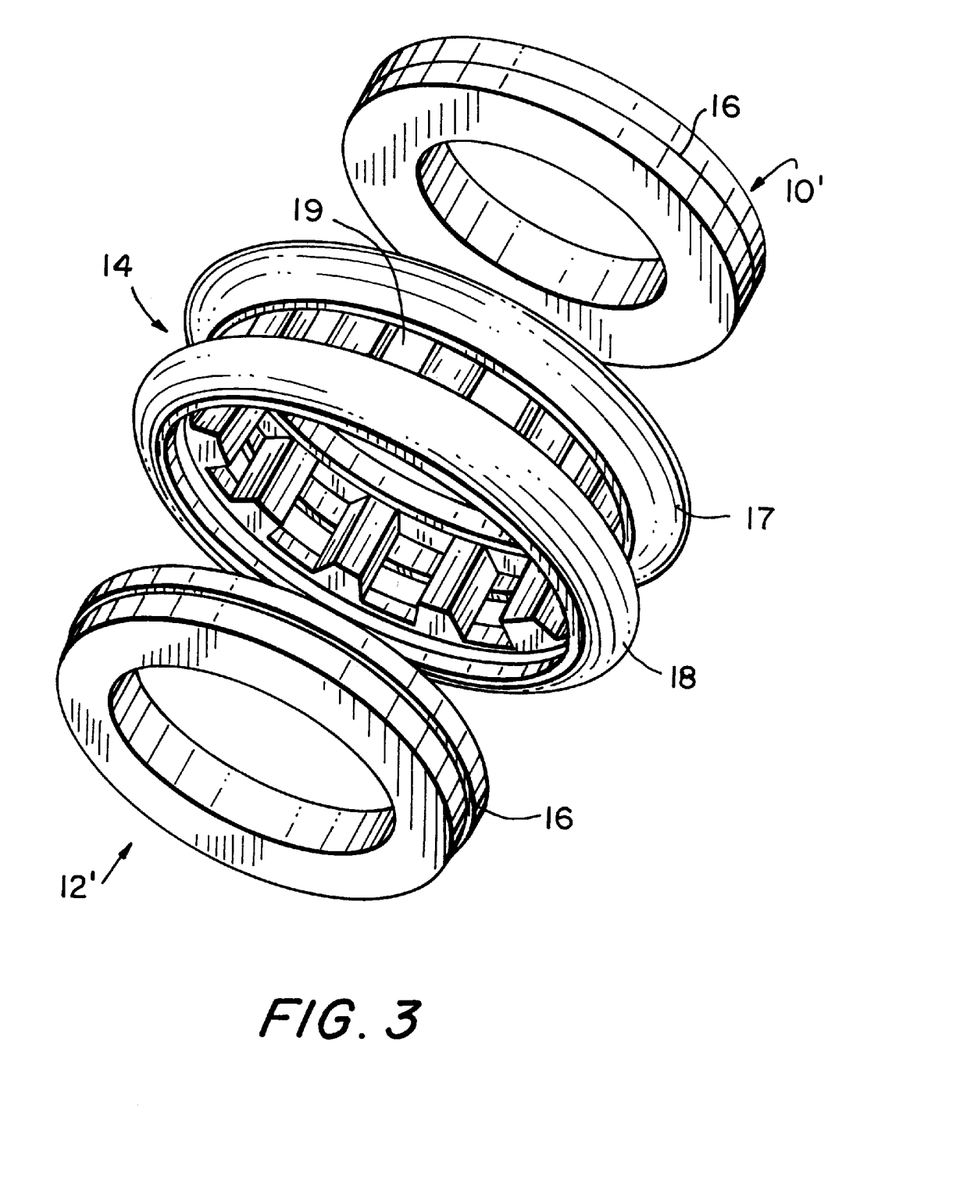
FIG. 3 is an exploded perspective view of the sealing device of FIG. 2 on a larger scale.

FIG. 3 is a perspective view of the sealing mechanism of FIG. 2 in the disassembled state. The sealing disc 10' can be seen above its seat in the support member 14. In order to improve the seat of this sealing disc 10' in the support member 14, the sealing disc 10' has at its outer side a step 16 which corresponds with a recess in the support member 14. The sealing disc 12' is constructed analogously. The support member 14 is composed of two annular parts 17, 18 which are connected to each other by a plurality of webs 19.

This ensures that the position of the two sealing discs relative to each other is secured in the axial direction and each individual of the two sealing discs is still movable independently of the other in the radial direction. The configuration of the sealing arrangement according to the invention shown in FIGS. 2 and 3 makes possible an easier replacement and a simple inspection of the condition of the sealing arrangement.

Suitable as materials for the support members 11, 13 and 14 are rubber or other medically safe elastomer materials, while the sealing discs 10, 12, 10', 12' are preferably of hard metal, steel, especially preferred of ceramic material or so-called heavy-duty synthetic materials or other materials which are optimized with respect to resistance to wear, or also of composite materials, or they are provided with coatings which are resistant to wear.

Experiments have shown that the inner areas of the end faces of the sealing discs which produce the actual sealing effect are not worn by the shoulders of the drill shafts; rather, the shoulders of the drills become smooth, similar to what happens during the break-in process of machine parts which slide on each other, and, when there are sealing problems in a drill which is used several times, the drill is removed and a tight seat is again achieved with the next drill.

The invention is not limited to the illustrated embodiment; rather, various modifications are possible. For example, it is not necessary to provide the diameter differences between the cylindrical surfaces 7 and 8 and between 8 and 8' in the illustrated manner. Instead of these step surfaces extending normally or perpendicularly of the drill axis, these step surfaces can also be constructed conically or spherically, but always symmetrically relative to the drill axis, in order to take into account the inclined positions of the drill 3 relative to the handpiece head 1. The size of the resulting angles can be selected so large that it is still just possible to speak of an axial seal; accordingly, the angle may be up to 45°, however, such large angles are not preferred.

In accordance with another further development of the present invention, it is possible to arrange from the top towards the bottom, in analogy to FIG. 2, first a plate spring, then an O-ring seated with its outer circumference against the wall of the cylindrical indentation, wherein the shoulder of a sealing disc which is somewhat thicker than the sealing disc shown in FIG. 2 rests against the inner contour of the O-ring, and wherein another plate spring, in turn, rests on the shoulder, and the other end of the plate spring rests against another analogous combination of an O-ring and a sealing disc.

Also essential for the operation is the radial mobility of each of the sealing discs which makes possible the adjustment to drill tolerances, inclined positions, out of center running, etc., without impairing the operation of the drill or the sealing means. This mobility is most easily achieved by constructing the support members of elastomer material, for example, rubber (caoutchouc).

While specific embodiments of the invention have been shown and described in detail to illustrate the inventive principles, it will be understood that the invention may be embodied otherwise without departing from such principles.

I claim:

1. A medical handpiece in combination with an internally cooled tool, the tool comprising a tool shaft with an axial hollow space, the tool shaft having a bore extending essentially in a radial direction for conducting cooling fluid into the axial hollow space, further comprising two sealing means arranged axially spaced apart from each other in a handpiece head for sealing the handpiece head relative to the tool shaft, wherein the bore is arranged between the two sealing means, wherein each sealing means is comprised of a sealing disc having a sealing surface in contact with the tool shaft, each sealing surface extending essentially in a normal, conical or spherical direction relative to the tool axis, wherein the tool shaft has in a sealing area thereof three different diameter portions, wherein a first and a second of the diameter portions and the second and a third diameter portions are each connected through a shoulder, wherein each of the sealing discs rests against one of the two shoulders, wherein at least one of the two sealing discs is mounted so as to be displaceable in the axial direction, and wherein each of the sealing discs is mounted so as to be movable in the handpiece head in the radial direction.

2. The handpiece according to claim 1, wherein the sealing discs are of a material which is harder than a material of the tool shaft at the shoulders thereof.

3. The handpiece according to claim 1, wherein the two sealing discs are mounted in a common support member arranged in an essentially cylindrical hollow space of the handpiece head, further comprising a spring acting in the axial direction on the support member.

4. The handpiece according to claim 3, wherein the support member is of an elastomer material.

5. The handpiece according to claim 3, wherein the spring is mounted on a side of the support member facing the handpiece head, and wherein the spring is a compression spring.

6. The handpiece according to claim 5, wherein the spring is a plate spring.

7. The handpiece according to claim 1, wherein the sealing discs are of a ceramic material or a hard metal.

8. The handpiece according to claim 1, wherein the sealing discs and the support member are of an elastomer material.

9. The handpiece according to claim 1, wherein the sealing discs and the support member are of rubber.

* * * * *